(12) United States Patent
Phillips

(10) Patent No.: US 12,138,458 B2
(45) Date of Patent: Nov. 12, 2024

(54) BRAIN STIMULATION USING SUBCRANIAL ELECTRODE AND SUBCUTANEOUS ELECTRODE

(71) Applicant: EPIC NEURO, INC., Fountain Valley, CA (US)

(72) Inventor: James William Phillips, Fountain Valley, CA (US)

(73) Assignee: Epic Neuro, Inc., Fountain Valley, CA (US)

( * ) Notice: Subject to any disclaimer, the term of this patent is extended or adjusted under 35 U.S.C. 154(b) by 788 days.

(21) Appl. No.: 17/374,796

(22) Filed: Jul. 13, 2021

(65) Prior Publication Data

US 2022/0008728 A1    Jan. 13, 2022

Related U.S. Application Data

(60) Provisional application No. 63/051,222, filed on Jul. 13, 2020.

(51) Int. Cl.
*A61N 1/36* (2006.01)
*A61B 5/00* (2006.01)
(Continued)

(52) U.S. Cl.
CPC .......... *A61N 1/36139* (2013.01); *A61B 5/372* (2021.01); *A61B 5/4836* (2013.01); *A61B 5/7257* (2013.01); *A61B 5/726* (2013.01); *A61B 5/7264* (2013.01); *A61N 1/0529* (2013.01); *A61N 1/0531* (2013.01);
(Continued)

(58) Field of Classification Search
CPC ................ A61N 1/0529; A61N 1/0531; A61N 1/36064; A61N 1/36067; A61N 1/36075; A61N 1/36096; A61N 1/36139; A61N 1/36175; A61N 1/37514; A61B 5/37; A61B 5/4836; A61B 5/7257; A61B 5/726; A61B 5/7264; A61B 2560/02
See application file for complete search history.

(56) References Cited

U.S. PATENT DOCUMENTS

| 6,205,359 B1 | 3/2001 | Boveja |
|---|---|---|
| 6,230,049 B1 | 5/2001 | Fischell et al. |

(Continued)

FOREIGN PATENT DOCUMENTS

| IN | 2020/37049555 A | 12/2020 |
|---|---|---|
| JP | 2009153974 A | 7/2009 |

(Continued)

OTHER PUBLICATIONS

Liu et al.; Titration of propofol for anesthetic induction and maintenance guided by the bispectral index: closed-loop versus manual control; The Journal of the Amercian Society of Anesthesiologists; 104(4); pp. 686-695; Apr. 2006.

(Continued)

*Primary Examiner* — Christopher A Flory
(74) *Attorney, Agent, or Firm* — Shay Glenn LLP

(57) ABSTRACT

A method is described, which provides electrical stimulation to a person, where the current flows from a subcranial electrode, through a target brain region, through a separate conductive path, and back to a subcutaneous electrode, and where the parameters of the electric current pulses are set to influence the resonant properties of the brain.

20 Claims, 9 Drawing Sheets

(51) Int. Cl.
 *A61B 5/372* (2021.01)
 *A61N 1/05* (2006.01)
 *A61N 1/375* (2006.01)

(52) U.S. Cl.
 CPC ..... *A61N 1/36175* (2013.01); *A61N 1/37514* (2017.08); *A61B 2560/02* (2013.01); *A61N 1/36064* (2013.01); *A61N 1/36067* (2013.01); *A61N 1/36075* (2013.01); *A61N 1/36096* (2013.01)

(56) References Cited

U.S. PATENT DOCUMENTS

| | | |
|---|---|---|
| 6,597,954 B1 | 7/2003 | Pless et al. |
| 7,228,171 B2 | 6/2007 | Lesser et al. |
| 7,346,391 B1 | 3/2008 | Osorio et al. |
| 7,440,806 B1 | 10/2008 | Whitehurst et al. |
| 7,853,323 B2 | 12/2010 | Goetz |
| 8,888,672 B2 | 11/2014 | Phillips et al. |
| 9,278,208 B1 | 3/2016 | Gilson et al. |
| 9,872,996 B2 | 1/2018 | Phillips |
| 10,565,574 B2 | 2/2020 | Powell |
| 10,780,286 B2 | 9/2020 | Phillips |
| 2002/0143365 A1 | 10/2002 | Herbst |
| 2003/0004428 A1 | 1/2003 | Pless et al. |
| 2003/0028072 A1 | 2/2003 | Fischell et al. |
| 2003/0125786 A1 | 7/2003 | Gliner et al. |
| 2005/0015128 A1 | 1/2005 | Rezal et al. |
| 2005/0070971 A1 | 3/2005 | Fowler et al. |
| 2005/0096703 A1 | 5/2005 | Sanders |
| 2006/0217782 A1 | 9/2006 | Boveja et al. |
| 2006/0229686 A1 | 10/2006 | Giftakis et al. |
| 2006/0241697 A1 | 10/2006 | Libbus et al. |
| 2007/0213629 A1 | 9/2007 | Greene |
| 2007/0225773 A1 | 9/2007 | Shen et al. |
| 2008/0033509 A1 | 2/2008 | Shalev et al. |
| 2008/0140149 A1 | 6/2008 | John et al. |
| 2008/0183225 A1 | 7/2008 | Adamski et al. |
| 2009/0005833 A1 | 1/2009 | Cameron et al. |
| 2009/0112278 A1 | 4/2009 | Wingeier et al. |
| 2009/0157157 A1 | 6/2009 | Schom et al. |
| 2009/0292344 A1 | 11/2009 | Lowry et al. |
| 2010/0125312 A1 | 5/2010 | Stevenson et al. |
| 2010/0168826 A1 | 7/2010 | Carpentier |
| 2010/0324623 A1 | 12/2010 | Tanaka et al. |
| 2010/0331925 A1 | 12/2010 | Peterson |
| 2011/0028859 A1 | 2/2011 | Chian |
| 2011/0046693 A1 | 2/2011 | Lee et al. |
| 2011/0112426 A1 | 5/2011 | Causevic |
| 2011/0112602 A1 | 5/2011 | Lee et al. |
| 2011/0137381 A1 | 6/2011 | Lee et al. |
| 2011/0166464 A1 | 7/2011 | Lee et al. |
| 2011/0213382 A1 | 9/2011 | Decre et al. |
| 2011/0218588 A1 | 9/2011 | Jung et al. |
| 2011/0237921 A1 | 9/2011 | Askin, III et al. |
| 2012/0274271 A1 | 11/2012 | Thompson et al. |
| 2013/0261706 A1 | 10/2013 | Mirro et al. |
| 2016/0121129 A1 | 5/2016 | Persson et al. |
| 2016/0144186 A1 | 5/2016 | Kaemmerer et al. |
| 2016/0199656 A1* | 7/2016 | Phillips ............... A61N 1/3606 607/45 |
| 2016/0367809 A1 | 12/2016 | Patel et al. |
| 2017/0021162 A1 | 1/2017 | Govea et al. |
| 2017/0035316 A1 | 2/2017 | Kuzniecky et al. |
| 2018/0085573 A1 | 3/2018 | Alam |
| 2018/0289311 A1 | 10/2018 | Phillips |
| 2018/0289969 A1 | 10/2018 | Malekkhosravi et al. |
| 2019/0001142 A1* | 1/2019 | Phillips ............. A61N 1/36171 |
| 2020/0030617 A1 | 1/2020 | Phillips |
| 2020/0269049 A1 | 8/2020 | Varkuti |
| 2020/0398061 A1 | 12/2020 | Phillips |
| 2021/0236807 A1 | 8/2021 | Tittelbach et al. |
| 2023/0256250 A1 | 8/2023 | Phillips |

FOREIGN PATENT DOCUMENTS

| | | |
|---|---|---|
| JP | 2017525545 A | 9/2017 |
| KR | 10-1645852 B1 | 8/2016 |
| WO | WO2008/005478 A2 | 1/2008 |
| WO | WO2016/030822 A1 | 3/2013 |
| WO | WO2015/021075 A1 | 2/2015 |
| WO | WO2016/053375 A1 | 4/2016 |

OTHER PUBLICATIONS

Shanechi et al.; A brain-machine interface for control of medically-induced coma; Plos Computational Biology.; 9(10); e1003284, 17 pages; Oct. 2013.
Chen et al.; Transcranial Doppler combined with quantitative EEG brain function monitoring and outcome prediction in patients with severe acute intracerebral hemorrhage; Critical Care; 22(1); pp. 1-9; Dec. 2018.
Phillips et al.; U.S. Appl. No. 18/566,284; entitled "Subcutaneous transcranial cortical electrotherapy stimulation method and device," filed Dec. 1, 2023.
Phillips et al.; U.S. Appl. No. 18/329,279 entitled "Brain stimulation device with targeted injectable drug delivery," filed Jun. 5, 2023.
Phillips.; U.S. Appl. No. 18/351,338 entitled "System, and methods for transcranial current loop brain simulation," filed Jul. 12, 2023.

* cited by examiner

BRAIN STIMULATION USING SUBCRANIAL ELECTRODE AND SUBCUTANEOUS ELECTRODE

CROSS REFERENCE TO RELATED APPLICATIONS

This application claims the benefit of priority of U.S. Provisional Application No. 63/051,222, filed Jul. 13, 2020, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Electric brain stimulation has been shown to be a potentially effective treatment for a number of brain disorders, including epilepsy, migraine, fibromyalgia, major depression, stroke rehabilitation, and Parkinson's disease, and is also used in electrocorticography and Cortical Stimulation Mapping (CSM). In epilepsy, the generally accepted treatment method involves locating the epileptic focus in the brain, which is found using EEG analysis of epileptiform discharges and resultant spike or seizure voltage fields at the scalp. The temporal lobe is often the location of epileptogenesis, though the position and orientation may vary between individuals. In treating major depression, the target is often the left dorsolateral prefrontal cortex. In treating migraine, the visual cortex or motor cortexes are generally targeted, as well as the occipital nerves. In stroke recovery for reduced limb movement, the area of the motor cortex associated with the limb is the usual target. Once the target site is located, electrical stimulation is applied to provide therapy for the specific indication.

Electric brain stimulation may be accomplished by several means. Repetitive Transcranial Magnetic Stimulation (rTMS) is a noninvasive technique that uses a coil to deliver a series of high energy magnetic pulses to the brain, thereby inducing current to flow in the cortex underneath the coil. rTMS has been shown to be effective in the treatment of major depression, and other mental disorders. However, it is not easily directed to a particular location, and involves a large, expensive device to generate the high current pulse to the coil. rTMS is not portable and requires a treatment administrator to deliver therapy to the subject.

Transcranial Direct Current Stimulation (tDCS) uses electrodes on the outside of the head to deliver small amounts of current to the brain. tDCS was originally used for stroke recovery, and has shown promise in the treatment of some mental disorders and for cognitive improvement. Electrodes are located near the region of interest for stimulation. The vast majority of current is shunted between the electrodes since the skull is a very effective electrical insulator. However, a portion of the current does result in intracerebral current flow, which may increase or decrease neuronal excitability and alter brain function. The exact method of action is unclear. tDCS current strength is limited due to the excitability of nerves in the scalp, which can cause discomfort to the subject if the current is set too high.

Vagus nerve stimulation involves electrically stimulating the vagus nerve in the neck of the subject. This can be done either using electrodes on the skin, which may involve painful sensation of the subject, or surgically implanting electrodes near the vagus nerve, generally with a power source implanted elsewhere in the body. This involves a significant surgical procedure and has shown efficacy in treatment of epilepsy and depression.

Deep brain stimulation (DBS) uses electrodes implanted and placed bilaterally into the basal ganglia, cerebellum, anterior principal nucleus, the centromedian nucleus, caudate nucleus, thalmic, or subthalmic region. Stimulation may also be delivered subcortically. Stimulus trains are delivered for treatment of a number of disorders, including epilepsy, Parkinson's disease, and major depression. DBS is generally a very invasive procedure, requiring a long lead that penetrates the skull with multiple electrodes near the tip. The procedure is considered major surgery and is not generally used unless other methods have been exhausted.

Direct cortical stimulation (DCS) is similar to DBS, except that the lead lies on the surface of the cortex, either subdural or epidural. The location of the electrodes is generally near the seizure foci. The electrodes are secured in place using sutures. This technique often involves removing a portion of the skull to gain access to the cortical surface, and possibly to make room for the power source. DCS has been shown to have efficacy in treatment of epilepsy and neuropathic pain.

It is possible to perform electrical stimulation of the brain utilizing a current loop through a conductive path involving a device that penetrates the skull at one or more points, along with a separate conductive path through the skull. Since the skull is highly resistive (approximately 80 times more resistive than the cerebrospinal fluid (CSF) around the brain), it acts as a good insulator. If the area around the device that penetrates the skull is filled with a resistive material, like silicone, then a current source through one device would not have a low impedance return path except through the other conductive path. The device could have an electrode at the tip, and the length, angle, and position of each device would allow for precise stimulation of any area of the brain. A second electrode could be located subcutaneously, so that the current return path would travel through or under the scalp.

SUMMARY

A method of treating a subject having an intrinsic frequency of neuronal firing in a specified EEG band is provided, comprising positioning a subcranial electrode and a subcutaneous electrode on opposite sides of a skull near a location on the skull of the subject, creating a separate conductive path at a separate location through the skull, and generating electric current pulses with the subcranial electrode and the subcutaneous electrode, the electric current pulses having a pulse frequency, a pulse shape, a pulse amplitude, a pulse width, and a duty cycle, wherein the electric current pulses flow from the subcranial electrode, through a target region of a brain of the subject, through the separate conductive path at the separate location through the skull, to the subcutaneous electrode, and adjusting the electric current pulses in order to move a Q-factor of the intrinsic frequency of neuronal firing in the specified EEG band of the subject toward a preselected Q-factor of the intrinsic frequency.

A method of treating a subject having an intrinsic frequency of neuronal firing in a specified EEG band is also provided, comprising: positioning a subcranial electrode and a subcutaneous electrode on opposite sides of a skull near a location on the skull of the subject; and creating a separate conductive path at a separate location through the skull; and generating electric current pulses with the subcranial electrode and the subcutaneous electrode, the electric current pulses having a pulse frequency, a pulse shape, a pulse amplitude, a pulse width, and a duty cycle, wherein the electric current pulses flow from the subcranial electrode, through a target region of a brain of the subject, through the separate conductive path at the separate location through the skull, to the subcutaneous electrode; and adjusting the electric current pulses in order to move the intrinsic frequency of neuronal firing in the specified EEG band of the subject toward a preselected intrinsic frequency.

In some embodiments, the method further includes recording an EEG between the subcranial electrode and the subcutaneous electrode; and determining the intrinsic frequency of neuronal firing in the specified EEG band using the recorded EEG.

In one embodiment, the pulse frequency is equal to the intrinsic frequency of neuronal firing in the specified EEG band of the subject.

In various embodiments, the pulse shape is a sine wave, a square wave, and/or a triangle wave.

In other embodiments, the pulse amplitude is rhythmically varying having a rhythmic frequency which is equal to the intrinsic frequency of neuronal firing in the specified EEG band of the subject.

In one embodiment, the method further comprises positioning a second subcranial electrode and a second subcutaneous electrode on opposite sides of the skull near a second location on the skull of the subject, further comprising recording a first EEG between the subcranial electrode and the subcutaneous electrode and recording a second EEG between the second subcranial electrode and the second subcutaneous electrode, wherein the intrinsic frequency of neuronal firing is an average of at least two local intrinsic frequencies in a specified EEG band, recorded at the location and the second location of the skull of the subject.

In some embodiments, the method further comprises calculating a fast fourier transform of the recorded EEG; and filtering the fast fourier transform such that a passband is the specified EEG band.

In one embodiment, determining the intrinsic frequency further comprises identifying a peak magnitude of the fast fourier transform.

In another embodiment, determining the intrinsic frequency further comprises applying wavelet transforms to the recorded EEG.

In yet another embodiment, determining the intrinsic frequency further comprises applying neural networks to the recorded EEG.

In some examples, determining the intrinsic frequency further comprises applying curve fitting to the recorded EEG.

In one embodiment, the preselected Q factor is defined as a ratio between the intrinsic frequency and a frequency bandwidth for which EEG energy is above one-half of a peak EEG energy.

A device is also provided, the device being configured for electrical stimulation of a subject's brain, the device comprising a first electrode adapted to be implanted under a scalp of the subject and under the subject's skull, a second electrode adapted to be implanted under the subject's scalp and outside the subject's skull, insulating material configured to electrically isolate the first electrode from the second electrode, a case, and a processor disposed within the case, the processor being configured to record an EEG between the first electrode and the second electrode, the processor being further configured to determine an intrinsic frequency of neuronal firing in a specified EEG band of the subject with the recorded EEG, and a generator disposed within the case and in electrical communication with the processor, the generator being adapted to adjust and deliver a current pulse waveform to the first electrode and the second electrode to move a Q-factor of the intrinsic frequency of neuronal firing in the specified EEG band of the subject towards a preselected Q-factor of the intrinsic frequency.

A device configured for electrical stimulation of a subject's brain, the device comprising: a first electrode adapted to be implanted under a scalp of the subject and under the subject's skull; a second electrode adapted to be implanted under the subject's scalp and outside the subject's skull; insulating material configured to electrically isolate the first electrode from the second electrode; and a case; and a processor disposed within the case, the processor being configured to record an EEG between the first electrode and the second electrode, the processor being further configured to determine an intrinsic frequency of neuronal firing in a specified EEG band of the subject with the recorded EEG; and a generator disposed within the case and in electrical communication with the processor, the generator being adapted to adjust and deliver a current pulse waveform to the first electrode and the second electrode to move the intrinsic frequency of neuronal firing in the specified EEG band of the subject towards a preselected intrinsic frequency.

In some embodiments, a pulse frequency of the waveform is equal to the intrinsic frequency of neuronal firing in the specified EEG band of the subject.

In various embodiments, a pulse shape of the waveform is a sine wave, a square wave, and/or a triangle wave.

In some embodiments, a pulse amplitude of the waveform is rhythmically varying having a frequency which is equal to the intrinsic frequency of neuronal firing in the specified EEG band of the subject.

In another embodiment, a pulse amplitude of the waveform is rhythmically varying having a frequency which is higher than the intrinsic frequency of neuronal firing in the specified EEG band of the subject.

In some embodiments, a pulse amplitude of the waveform is rhythmically varying having a frequency which is lower than the intrinsic frequency of neuronal firing in the specified EEG band of the subject.

In one example, the processor is configured to determine the intrinsic frequency by: calculating a fast fourier transform of the recorded EEG; and filtering the fast fourier transform such that a passband is the specified EEG band.

In another embodiment, the processor is further configured to determine the intrinsic frequency by identifying a peak magnitude of the fast fourier transform.

In some embodiments, the processor is further configured to determine the intrinsic frequency by applying wavelet transforms to the recorded EEG.

In another embodiment, the processor is further configured to determine the intrinsic frequency by applying neural networks to the recorded EEG.

In some examples, the processor is further configured to determine the intrinsic frequency by applying curve fitting to the recorded EEG.

In another embodiment, the preselected Q factor is defined as a ratio between the intrinsic frequency and a frequency bandwidth for which EEG energy is above one-half of a peak EEG energy.

DETAILED DESCRIPTION

Figure 1:
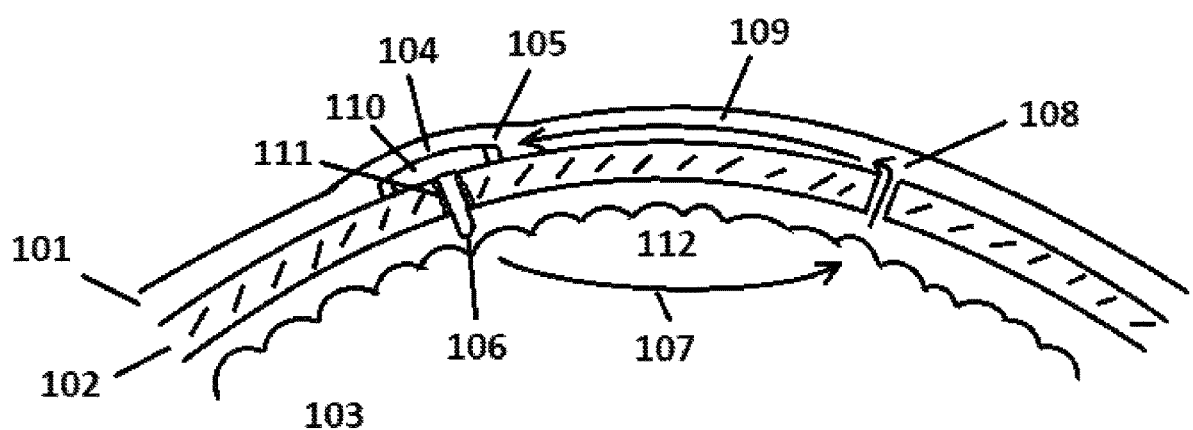
FIG. 1 is a drawing showing one aspect of the method, in which a stimulator is implanted with a subcutaneous/subcranial electrode pair, and electric pulses form a current loop through a separate conductive path.

While certain embodiments have been provided and described herein, it will be readily apparent to those skilled in the art that such embodiments are provided by way of example only. It should be understood that various alternatives to the embodiments described herein may be employed, and are part of the invention described herein.

Provided herein are systems and methods for applying electrical current stimulation to the brain of a person through one or more conductive paths that proceed through the skull, using the skull's high impedance to create a current loop, which allows current to flow interior and exterior to the skull and through at least one stimulation target.

In one aspect of the disclosure, the system can comprise a device that includes a subcutaneous electrode and a subcranial electrode. A method can comprise treating a subject having an intrinsic frequency of neuronal firing in a specified EEG band, comprising: (a) Positioning the subcranial electrode and the subcutaneous electrode on opposite sides of a skull near a location on the skull of the subject; and (b) creating a separate conductive path at a separate location through the skull; and (c) generating electric current pulses between the subcranial electrode and the subcutaneous electrode, the electric current pulses having a pulse frequency, a pulse shape, a pulse amplitude, a pulse width, and a duty cycle, wherein the electric current pulses flow from the subcranial electrode, through a target region of a brain of the person, through the separate conductive path through the skull, to the subcutaneous electrode; and (d) adjusting the electric current pulses in order to move a frequency, phase, coherence, or Q-factor of the intrinsic frequency of neuronal firing in the specified EEG band of the subject toward a preselected frequency, phase, coherence, or Q-factor of the intrinsic frequency using the electric current pulses.

The subcutaneous electrode can be positioned either inside, on the outside, or above the skull, and can be configured to maintain an electrical connection to the scalp of the subject. The subcranial electrode can be positioned either inside, on the outside, or below the skull, and can be configured to maintain an electrical connection to the brain, dura, or cerebrospinal fluid. In one embodiment, the two electrodes are positioned on opposite sides of the same location on the skull. The subcranial electrode may be part of a device, which can be inserted through a burr-hole in the skull. An electrically insulating seal may be positioned between the outside of the device and the wall of the burr-hole, in order to prevent fluid transfer between the subcranial region and the scalp, and may also prevent a direct electrical path between the subcranial electrode and the subcutaneous electrode.

The device can comprise a subcranial electrode and a subcutaneous electrode. When the device is implanted, the subcranial electrode may be inserted through a burr-hole in the skull, while the subcutaneous electrode maintains an electrical connection to the scalp of the subject. The device may be conductive, so as to create a conductive path through the skull. However, due to an electrically insulating seal between the device and the wall of the burr-hole, the subcranial electrode is electrically isolated from the subcutaneous electrode so that no direct low-impedance electrical path exists between the subcranial electrode and subcutaneous electrode. The skull has a relatively high impedance to electric current flow. In order to provide electrical stimulation to a target region of the brain, an electrically conductive path may be created through the skull at a separate location. This allows a current-loop to be formed when stimulation pulses are administered between the subcranial electrode and subcutaneous electrode.

The current pulses delivered by the device each have a pulse shape, which may be monophasic or biphasic. Although the exact pulse shape may be any shape, preferably the shape is square, triangular, or sinusoidal. It is also possible to form a pulse as a combination of shapes. The pulses have a pulse amplitude, which depends on the magnitude of electric current generated between the subcranial and subcutaneous electrodes. The pulses have a pulse frequency, pulse width and a duty cycle. For a particular frequency, the pulse width and duty cycle determine what percentage of the pulse period electrical stimulation is active.

In order to affect the natural resonance of the brain, an EEG may be recorded by the device or by an external EEG recording device and an intrinsic frequency of a specified EEG band may be determined. Additionally, a Q-factor may be calculated, which measures frequency selectivity of the specified EEG band. The pulse frequency may be adjusted in order to influence the Q-factor toward a preselected Q-factor.

The preselected Q-factor may be an average Q-factor of the intrinsic frequency of a healthy population database. If the Q-factor of the intrinsic frequency is higher than the average Q-factor of the intrinsic frequency of the healthy population database, the pulse frequency, pulse amplitude, pulse shape, pulse width, or pulse duty cycle may be set so as to tune down the Q-factor of the intrinsic frequency of the subject. If the Q-factor of the intrinsic frequency is lower than the average Q-factor of the intrinsic frequency of the healthy population database, the pulse frequency, pulse amplitude, pulse shape, pulse width, or pulse duty cycle may be set so as to tune up the Q-factor of the intrinsic frequency of the subject.

In one aspect of this disclosure, the intrinsic frequency of neuronal firing in a specified EEG band is determined using an EEG recorded between the subcranial electrode and the subcutaneous electrode. Alternately, the EEG may be recorded externally through a wearable cap and scalp electrodes, or with a different EEG recording device with implanted electrodes.

In some embodiments, EEG can be recorded during stimulation, or alternatively when stimulation is inactive. When the EEG is recorded between the subcranial electrode and the subcutaneous electrode, the recording may be performed one time, with the intrinsic frequency of neuronal firing from that recording being used for multiple treatment sessions. Alternately, the EEG could be recorded before each treatment session, with the intrinsic frequency updated based on the newly recorded EEG. The intrinsic frequency could be set to the one calculated using the most recently recorded EEG, or the intrinsic frequency could be calculated using multiple EEG recordings. For example, the new intrinsic frequency could be set to the average of two or more of the intrinsic frequencies calculated previously.

Since the electric current pulses are deterministic in nature, in some embodiments the intrinsic frequency, pulse amplitude, pulse shape, pulse width, or pulse duty cycle are updated continuously throughout the session, or alternatively treatment may be paused for a short period of time in order to record EEG and update the calculated intrinsic frequency.

In one aspect, the pulse frequency is equal to the intrinsic frequency of neuronal firing in the specified EEG band of the person. By setting the pulse frequency to the intrinsic frequency, the system maximizes the resonant properties of the brain's neuronal activity to have the largest impact. Alternately, the pulse frequency could be set higher than the intrinsic frequency. Alternately, the pulse frequency could be set lower than the intrinsic frequency. This may assist in either shifting the intrinsic frequency of neuronal firing toward or away from the pulse frequency, or reduce the Q-factor of the intrinsic frequency. Alternately, the pulse frequency could shift periodically within a range around the intrinsic frequency. By shifting periodically, it may be possible to affect the resonant properties of smaller groups of neurons which may have an intrinsic frequency that is different from the larger group that contributes to the overall intrinsic frequency. For example, the pulse frequency could shift by increments across the entire EEG band. In another example, the pulse frequency could stay at specific frequency values based on the frequency spectrum of the EEG within the band.

In one aspect, the pulse amplitude is sinusoidally variable, having a sinusoidal frequency. It may require a less complicated electronics to generate pulses that vary sinusoidally rather than generating a continuous sinusoid. In one aspect, the sinusoidal frequency is equal to the intrinsic frequency of neuronal firing in the specified EEG band of the person. By setting the sinusoidal frequency to the intrinsic frequency, the system maximizes the resonant properties of the brain's neuronal activity to have the largest impact. Alternately, the sinusoidal frequency could be set higher than the intrinsic frequency. Alternately, the sinusoidal frequency could be set lower than the intrinsic frequency. This may assist in either shifting the intrinsic frequency of neuronal firing toward or away from the sinusoidal frequency, or reduce the Q-factor of the intrinsic frequency. Alternately, the sinusoidal frequency could shift periodically within a range around the intrinsic frequency. By shifting periodically, it may be possible to affect the resonant properties of smaller groups of neurons which may have an intrinsic frequency that is different from the larger group that contributes to the overall intrinsic frequency. For example, the sinusoidal frequency could shift by increments across the entire EEG band. In another example, the sinusoidal frequency could stay at specific frequency values based on the frequency spectrum of the EEG within the band.

The pulse shape may be chosen to best affect neuronal firing. In one aspect, the pulse shape is a sine wave. In another aspect, the pulse shape is a square wave. In another aspect, the pulse shape is a triangle wave.

The intrinsic frequency may be based on the EEG recorded between two electrodes, as in a single EEG channel, or may be based on the EEG recorded between more than two electrodes, as in two or more EEG channels. In one aspect, the intrinsic frequency of neuronal firing is an average of two or more local intrinsic frequencies in a specified EEG band, recorded at physically separate locations on or above the skull of the subject. When averaging two or more local intrinsic frequencies, the EEG recordings could be made using multiple pairs of implanted electrodes. It may also be made using multiple scalp electrodes that are external to the body.

FIG. 1 shows one embodiment in which a thumbtack-shaped device 104 is implanted beneath the scalp 101 of a subject and comprises a case 110, a probe-shaped subcranial electrode 106 which is inserted into a drill-hole in the skull 102, and a subcutaneous ring electrode around the case 105. In one embodiment, the subcranial electrode can comprise a screw adapted to be screwed into the subject's skull. The system can further comprise an electrically insulating seal 111 filling the space between the device and the interior wall of the burr-hole, which prevents fluid flow and electric current flow around the subcranial electrode. The case 110 can rest on the surface of the skull and can comprise an electric current or voltage pulse generator to generate electric current pulses between the subcranial electrode and the subcutaneous electrode. Due to the high impedance of the skull 102, a majority of the electric current is forced to follow a path 107 which proceeds from the subcranial electrode through a target region 112 of the brain 103, through a conductive path 108 at a separate location in the skull, and back along path 109 underneath the scalp to the subcutaneous ring electrode 105.

In one embodiment, the device 104 can include electronics, such as a voltage or current pulse generator, configured to generate electric current waveforms between the subcranial electrode 106 and the subcutaneous ring electrode 105. The device can further include a power source such as a battery or a capacitor, or alternatively, can be powered externally with wireless power transfer (e.g., inductive coupling). The electronics can further include one or more processors, microcontrollers, or CPUs configured to control operation of the device and process and/or evaluate data sensed by the electrodes. In some embodiments, the electronics can further include memory configured to store recorded data and/or instructions related to the operation of the device and/or sensed parameters (e.g., EEG) of the patient. The electronics can be disposed or positioned within the case 110, for example. In some embodiments, the electronics are positioned external to the device and to the subject. In these embodiments, current pulses may be created external to the body, with percutaneous leads transmitting the current pulses to the subcutaneous/subcranial electrodes.

The device can be configured to record EEG and automatically determine the intrinsic frequency from the EEG recording and specify the pulse frequency, pulse amplitude, pulse shape, pulse width, or pulse duty cycle, and other parameters. The recorded EEG may also be transmitted wirelessly to an external module, such as a mobile device running a software application, where the software application determines the intrinsic frequency and specifies the pulse frequency, pulse amplitude, pulse shape, pulse width, or pulse duty cycle, and other parameters, and transmits the parameters to the device.

Figure 2:
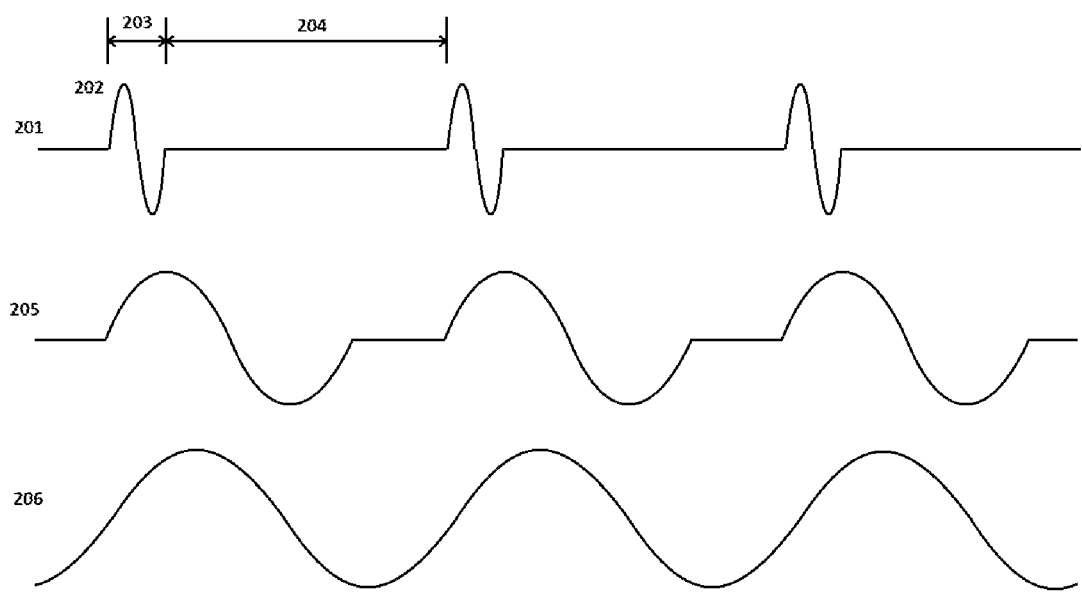
FIG. 2 is a drawing of different possible duty cycles for a series of sinusoidal magnetic pulses. Three possible duty cycles are shown.

FIG. 2 shows exemplary waveforms that can be delivered by the device of FIG. 1 using a sinusoidal pulse. The waveforms have the same pulse frequency, but different pulse width and duty cycle. The first waveform (201) comprises a series of sinusoidal pulses (202), each with a pulse width (203) and interval between pulses (204). The duty cycle for the waveform can be calculated as (pulse width)/(pulse width+interval between pulses). In this figure, the duty cycle of the first waveform is approximately 10%. The second waveform (205) has a duty cycle of approximately 75%. The third waveform (206) has a duty cycle of 100%. In this case, the waveform is a continuous sine wave.

A sine wave is especially effective at taking advantage of the resonant properties of neuronal firing, since all the energy of a sine wave is contained in or near a single frequency, whereas the first two waveforms (201 and 205) provide stimulation with energy that is spread across a wide frequency spectrum. Therefore, the preferred embodiment of the present invention comprises a continuous sine wave.

Figure 3:
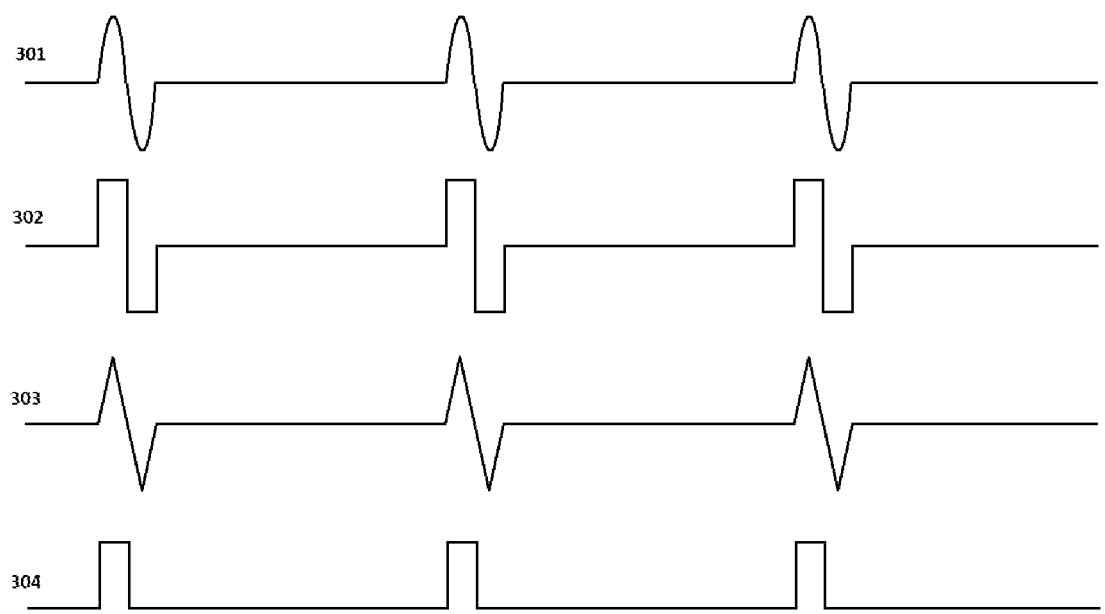
FIG. 3 is a drawing showing various pulse wave shapes. Included are bi-phasic sinusoidal, bi-phasic square, bi-phasic triangle, and mono-phasic square.

FIG. 3 shows example waveforms using various pulse shapes. The first waveform (301) uses a sinusoidal pulse. The second waveform (302) uses a bi-phasic square pulse. The third waveform (303) uses a bi-phasic triangle pulse. The fourth waveform (304) uses a mono-phasic square pulse. Each of these pulse shapes has different effects on neuronal firing, and may be generated using different electronics. For example, a sinusoidal pulse may be generated using a standard LC oscillator. A square pulse may be generated using a gated current or voltage source, with a polarity switch. A triangle pulse may be generated by charging a capacitor with a current source.

Figure 4:
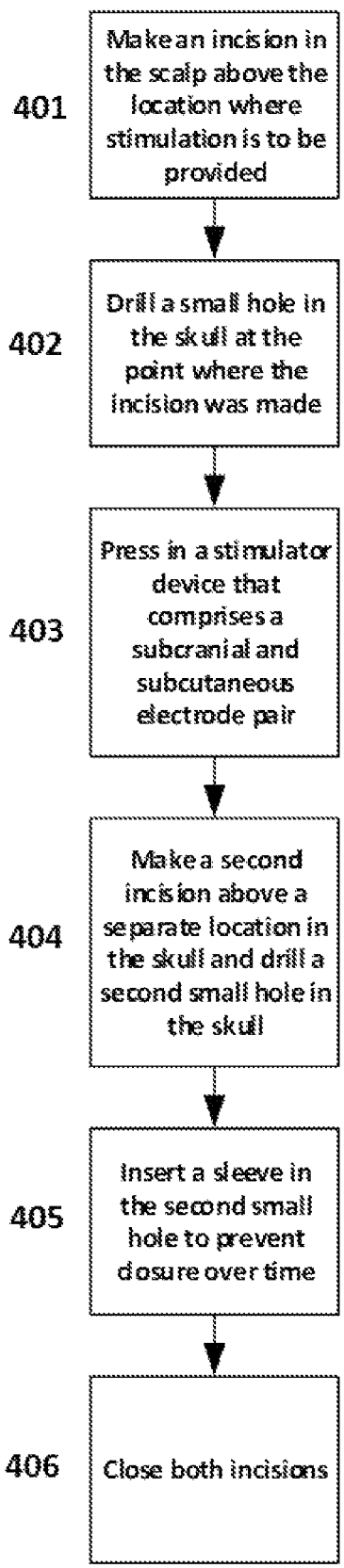
FIG. 4 is a flow chart describing the implantation procedure for a current-loop device.

FIG. 4 shows a flowchart of the process whereby a device such as was shown in FIG. 1 may be implanted in a subject. Initially, at step 401, a surgeon makes an incision in the scalp (scalp 101 of FIG. 1) where stimulation is to be provided. At step 402, the surgeon drills a small hole in the skull (skull 102 of FIG. 1) at the point where the incision was made. A scan may be performed before the surgical procedure to determine skull thickness so as to avoid any damage to the dura or brain tissue. At step 403, the surgeon presses the stimulator device (device 104 of FIG. 1) into place, so that the subcranial electrode (subcranial electrode 106 of FIG. 1) is within or beneath the skull and the subcutaneous electrode (subcutaneous electrode 105 of FIG. 1) is above the skull. In some embodiments, the subcranial electrode may be kept short so that it does not penetrate the dura. In other embodiments, it may also be long enough to penetrate the dura and the brain in order to stimulate deeper structures. At step 404, the surgeon makes a second incision at a separate location in the scalp, away from the implanted device, and drills a second small hole in the skull at the second location. At step 405, to prevent the skull from closing the second hole over time, the surgeon may optionally implant a sleeve to press against the sides of the hole, preventing closure and allowing an electrical connection between the inside and outside of the skull at the second location. Alternately, a conductive material, such as stainless steel or titanium may be used to fill the hole. At step 406, the surgeon may close both incisions. The location of the electrodes and second conductive path may be chosen so that the electric pulses flow through the target region of the brain (target region 111 of brain 103 in FIG. 1).

Figure 5:
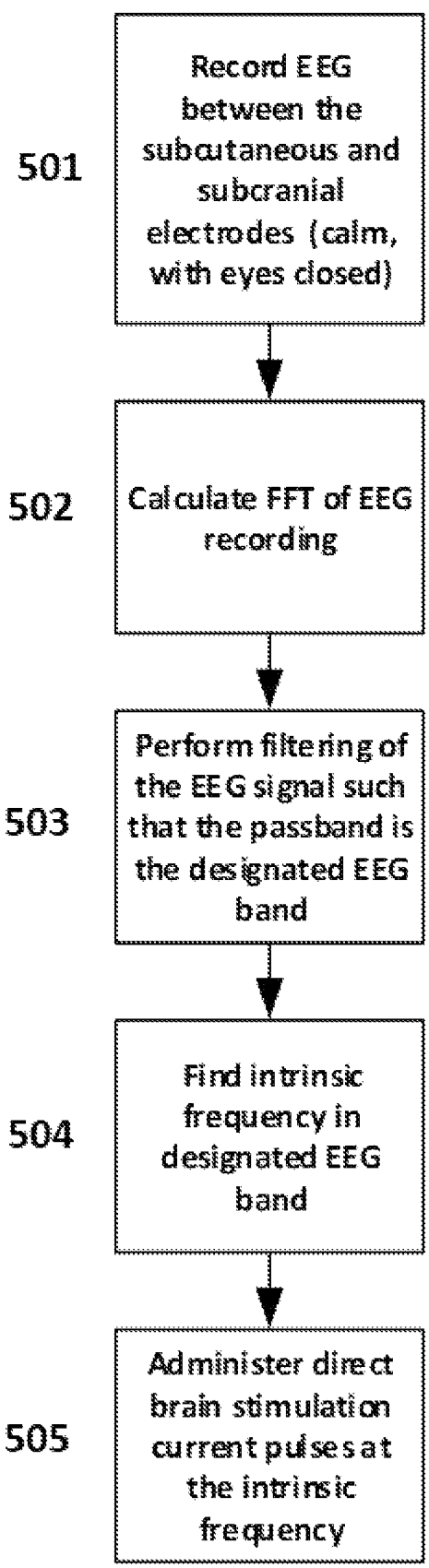
FIG. 5 is a flow chart showing an example procedure to calculate the intrinsic frequency of neuronal firing, and setting the electric current pulse frequency equal to the intrinsic frequency.

FIG. 5 shows an example of a flowchart of the process whereby EEG is recorded and the proper stimulation is provided with a device such as the device of FIG. 1. In this example, at step 501, an EEG is recorded between the subcutaneous and subcranial electrodes (subcutaneous electrode 105 and subcranial electrode 106 of FIG. 1) and optionally stored in memory on the device. During this period, the person should preferably be calm and relaxed, with eyes closed, in order to record as clean an EEG as possible, and to ensure the neurons fire as rhythmically as possible. At step 502, a Fast Fourier Transform (FFT) of the EEG recording is calculated (such as with the electronics/processors of the device of FIG. 1). At step 503, filtering of the FFT may be performed such that the passband is the designated EEG band. In this band, at step 504, the intrinsic peak frequency may be found as the frequency with an FFT magnitude that is the peak value. Other methods also exist to find the intrinsic frequency. In other embodiments, the device can use wavelet transforms, curve fitting, neural networks, optimization techniques, and other methods. Once the intrinsic frequency is found, the Q-factor may also be calculated by the electronics of the device, and the electric current pulses are then delivered by the device using parameters to affect the Q-factor, frequency, phase, or coherence of neuronal foring. For example, at step 505, the current pulses may be set to the intrinsic frequency, in order to increase Q-factor.

In some examples, the device can be used to stimulate the neurons, then stimulation can be stopped and the device can be used to record EEG for a time period. The intrinsic frequency may be found as the stimulation frequency that results in the greatest ringing effect in EEG after stimulation is stopped. The ringing effect may be defined as the length of time that the EEG waveform remains highly rhythmic or oscillatory after stimulation is removed.

Figure 6:
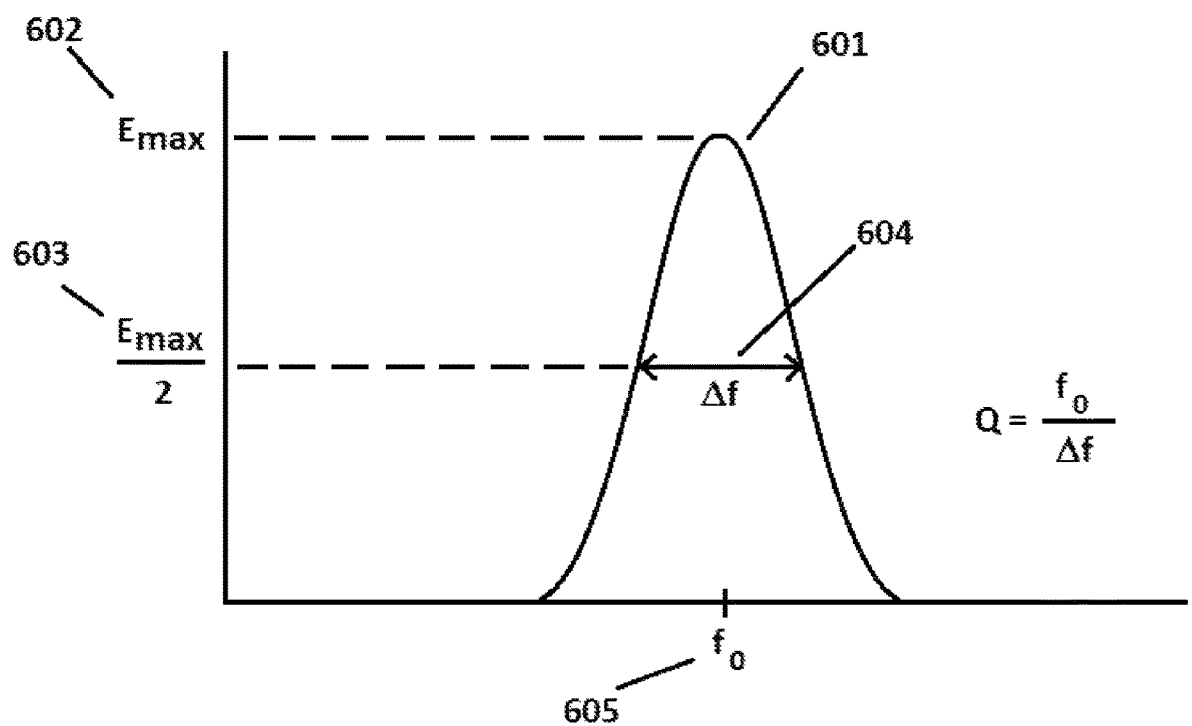
FIG. 6 is a drawing showing how Q-factor is defined, which demonstrates that a higher Q-factor indicates greater frequency selectivity of neuronal firing.

FIG. 6 one example of calculating the Q-factor as used above in steps 504 and 505 of FIG. 5. As mentioned above, the Q-factor can be calculated by the device, such as by the processor(s) of the device. FIG. 6 shows a sample graph of the frequency distribution of the energy of an EEG signal 601. It can be seen that the frequency range, $\Delta f$ can be defined as the frequency bandwidth for which the energy is above one-half the peak energy 603. The frequency $f_0$ is defined as the intrinsic frequency 605 in the specified band. The Q-factor is defined as the ratio of $f_0/\Delta f$. As can be seen, when $\Delta f$ decreases for a given $f_0$, the Q-factor will increase. This can occur when the peak energy $E_{max}$ (602) of the signal increases or when the bandwidth (604) of the EEG signal decreases.

The current pulses may be generated by a voltage source or a current source. As described above, the voltage source or the current source can be integrated into the device to make it fully implantable, or can be separate from the device and connected to the device with leads. Multiple stimulator devices may be implanted, each generating its own current pulses. If current sources are used to create the current pulses, it may be necessary for one of the conductive paths to not comprise a stimulator device, since current sources do not function well when connected in series. If voltage sources are used to create the current pulses, then all conductive paths could have stimulator devices inserted, which amounts to a series connection of voltage sources.

Figure 7:
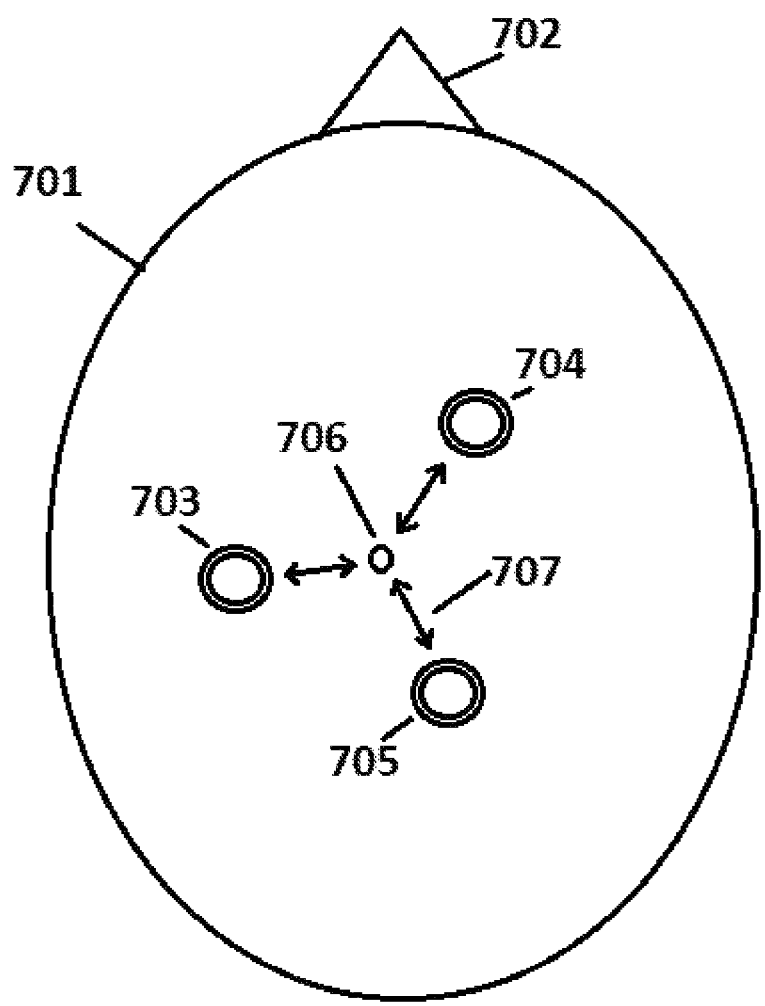
FIG. 7 is a drawing showing three devices, each incorporating a subcutaneous/subcranial electrode pair, with current pulses traveling through a centrally located conductive path through the skull.

FIG. 7 shows a head of a subject 701, with nose 702 for reference, and an example system in which three subcutaneous electrodes 703, 704, and 705 are configured around a conductive path through the skull 706. Each subcutaneous electrode is paired with a subcranial electrode (not shown, but described above), which is located underneath the subcutaneous electrode on the opposite side of the skull. The subcutaneous/subcranial electrode pairs are part of an implantable stimulator device as was shown in FIG. 1. Each of the devices generate electric current pulses, and due to the high impedance of the skull, the current 707 is forced to flow from the subcranial electrode, through the target region in the brain, along the conductive path, and back to the subcutaneous electrode. The devices may each record an EEG and calculate an intrinsic frequency of neuronal firing in an EEG band, and configure the pulses to affect the local Q-factor around each device. Alternately, the intrinsic frequency calculations from each of the EEG recordings may be averaged together, with all devices configured in the same way. This allows the Q-factor of the intrinsic frequency of neuronal firing of the regions as a whole to be affected, instead of targeting the local region around each individual device. The pulses from the devices could be synchronized so they all fire with a fixed phase relationship, or they may time their pulses independently from each other.

Figure 8:
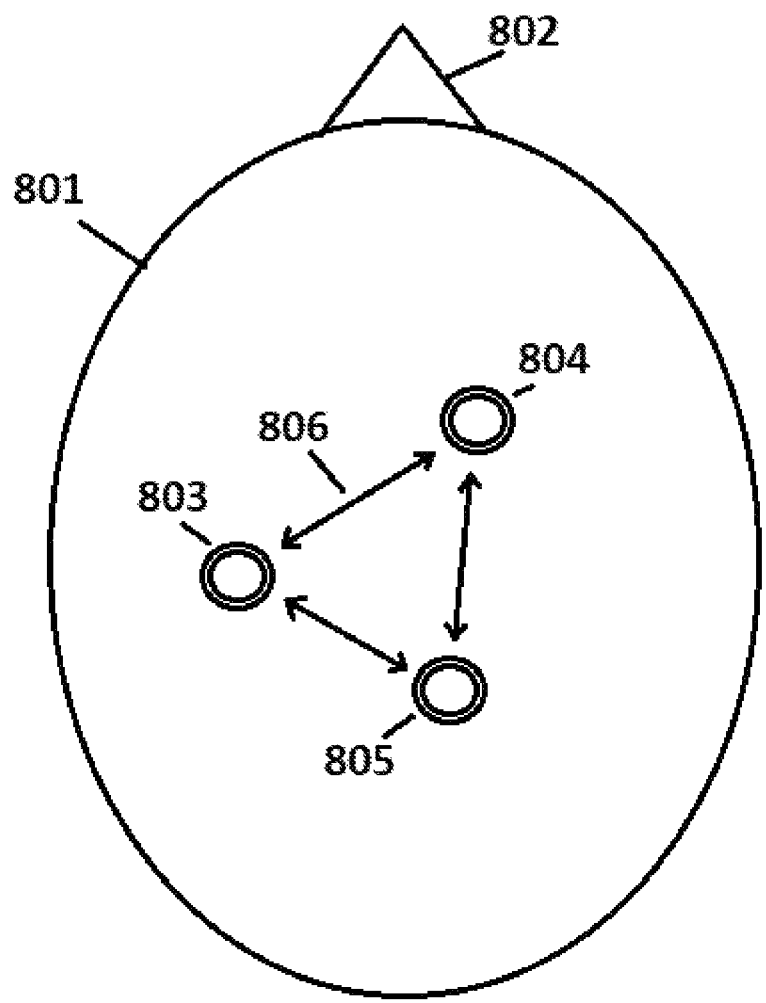
FIG. 8 is a drawing showing three devices, where a voltage source is used to create the electric current pulses, and there is no centrally located conductive path, so the electric current pulses are forced to travel through other devices.

FIG. 8 shows a head of a subject 801, with nose 802 for reference, and an alternate example system, which does not include the separate conductive path through the skull, as was shown in FIG. 7. The three subcutaneous electrodes 803, 804, and 805 are configured so that current 806 will flow between the implanted devices. In this case, the devices may use a voltage source to generate the electric current pulse instead of a current source. When a device generates a voltage pulse between the subcutaneous/subcranial electrode pair, the current flows through the conductive path created by other devices. Voltage pulses from different devices may be synchronized with each other, which may increase current flow between devices.

Figure 9:
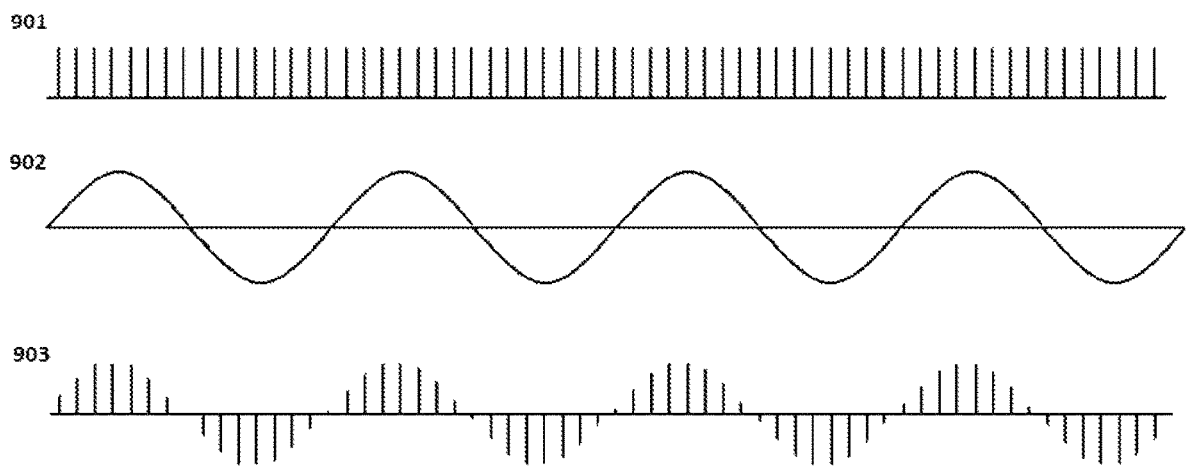
FIG. 9 is a drawing showing an example means of producing stimulation pulses with sinusoidally varying amplitude.

FIG. 9 shows an example pulse train 903 in which the amplitude of pulses is rhythmically varying, having a defined rhythmic frequency. The pulse train may be thought of as a constant amplitude pulse train having a pulse frequency 901 multiplied by a sine wave 902 having a rhythmic frequency which is significantly lower than the pulse frequency. For example, in FIG. 9, the pulse frequency is 160 Hz, and the rhythmic frequency is 9.9 Hz. This allows the stimulation to include energy at or near the rhythmic frequency, while still allowing for high frequency pulsed stimulation. In general, pulsed stimulation may be easier to implement than pure sinusoidal stimulation. The rhythmic frequency may be set to influence the intrinsic frequency of a specified EEG band. In this example, the amplitude is rhythmically variable with an envelope or limit in the shape of a sine wave. In other aspects, the amplitude may be rhythmically varying where the envelope or limit implements another shape, such as a triangle wave, square wave, or some other shape wave.

It will be understood by those of skill in the art that numerous and various modifications can be made without departing from the spirit of the present invention. Therefore, it should be clearly understood that the forms of the present invention are illustrative only and are not intended to limit the scope of the present invention.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating a subject having an intrinsic frequency of neuronal firing in a specified EEG band, comprising:
   positioning a subcranial electrode and a subcutaneous electrode on opposite sides of a skull near a location on the skull of the subject;
   creating a separate conductive path at a separate location through the skull;
   generating electric current pulses with the subcranial electrode and the subcutaneous electrode, the electric current pulses having a pulse frequency, a pulse shape, a pulse amplitude, a pulse width, and a duty cycle, wherein the electric current pulses flow from the subcranial electrode, through a target region of a brain of the subject, through the separate conductive path at the separate location through the skull, to the subcutaneous electrode; and
   adjusting the electric current pulses in order to move a Q-factor of the intrinsic frequency of neuronal firing in the specified EEG band of the subject toward a preselected Q-factor of the intrinsic frequency.

2. The method of claim 1 further comprising:
   recording an EEG between the subcranial electrode and the subcutaneous electrode; and
   determining the intrinsic frequency of neuronal firing in the specified EEG band using the recorded EEG.

3. The method of claim 1 wherein the pulse frequency is equal to the intrinsic frequency of neuronal firing in the specified EEG band of the subject.

4. The method of claim 1 wherein the pulse shape is selected from the group consisting of a sine wave, a square wave, and a triangle wave.

5. The method of claim 1 wherein the pulse amplitude is rhythmically varying having a rhythmic frequency which is equal to the intrinsic frequency of neuronal firing in the specified EEG band of the subject.

6. The method of claim 1, further comprising positioning a second subcranial electrode and a second subcutaneous electrode on opposite sides of the skull near a second location on the skull of the subject, further comprising recording a first EEG between the subcranial electrode and the subcutaneous electrode and recording a second EEG between the second subcranial electrode and the second subcutaneous electrode, wherein the intrinsic frequency of neuronal firing is an average of at least two local intrinsic frequencies in a specified EEG band, recorded at the location and the second location of the skull of the subject.

7. The method of claim 2, further comprising:
   calculating a fast fourier transform of the recorded EEG; and
   filtering the fast fourier transform such that a passband is the specified EEG band.

8. The method of claim 7, wherein determining the intrinsic frequency further comprises identifying a peak magnitude of the fast fourier transform.

9. The method of claim 7, wherein determining the intrinsic frequency further comprises applying wavelet transforms to the recorded EEG.

10. The method of claim 7, wherein determining the intrinsic frequency further comprises applying neural networks to the recorded EEG.

11. The method of claim 7, wherein determining the intrinsic frequency further comprises applying curve fitting to the recorded EEG.

12. The method of claim 1, wherein the preselected Q factor is defined as a ratio between the intrinsic frequency and a frequency bandwidth for which EEG energy is above one-half of a peak EEG energy.

13. A method of treating a subject having an intrinsic frequency of neuronal firing in a specified EEG band, comprising:
    positioning a subcranial electrode and a subcutaneous electrode on opposite sides of a skull near a location on the skull of the subject;
    creating a separate conductive path at a separate location through the skull;
    generating electric current pulses with the subcranial electrode and the subcutaneous electrode, the electric current pulses having a pulse frequency, a pulse shape, a pulse amplitude, a pulse width, and a duty cycle, wherein the electric current pulses flow from the subcranial electrode, through a target region of a brain of the subject, through the separate conductive path at the separate location through the skull, to the subcutaneous electrode; and
    adjusting the electric current pulses in order to move the intrinsic frequency of neuronal firing in the specified EEG band of the subject toward a preselected intrinsic frequency.

14. The method of claim 13 further comprising:
    recording an EEG between the subcranial electrode and the subcutaneous electrode; and
    determining the intrinsic frequency of neuronal firing in the specified EEG band using the recorded EEG.

15. The method of claim 13 wherein the pulse frequency is equal to the intrinsic frequency of neuronal firing in the specified EEG band of the subject.

16. The method of claim 13 wherein the pulse shape is selected from the group consisting of a sine wave, a square wave, and a triangle wave.

17. The method of claim 13 wherein the pulse amplitude is rhythmically varying having a rhythmic frequency which is equal to the intrinsic frequency of neuronal firing in the specified EEG band of the subject.

18. The method of claim 13, further comprising positioning a second subcranial electrode and a second subcutaneous electrode on opposite sides of the skull near a second location on the skull of the subject, further comprising recording a first EEG between the subcranial electrode and the subcutaneous electrode and recording a second EEG between the second subcranial electrode and the second subcutaneous electrode, wherein the intrinsic frequency of neuronal firing is an average of at least two local intrinsic frequencies in a specified EEG band, recorded at the location and the second location of the skull of the subject.

19. The method of claim 14, further comprising:
    calculating a fast fourier transform of the recorded EEG; and
    filtering the fast fourier transform such that a passband is the specified EEG band.

20. The method of claim 19, wherein determining the intrinsic frequency further comprises identifying a peak magnitude of the fast fourier transform.

* * * * *